(12) United States Patent
Borredon et al.

(10) Patent No.: US 7,022,845 B2
(45) Date of Patent: Apr. 4, 2006

(54) MONOMETHYLATION OF NITROGENEOUS HETEROCYCLES

(75) Inventors: Elisabeth Borredon, Tournefeuille (FR); Berhard Chabaud, Carpentras (FR); Antoine Gaset, Toulouse (FR); Sophie Thiebaud-Roux, L'Union (FR); Samedy Ouk, Toulouse (FR)

(73) Assignee: Group SNPE, (FR)

( * ) Notice: Subject to any disclaimer, the term of this patent is extended or adjusted under 35 U.S.C. 154(b) by 62 days.

(21) Appl. No.: 10/632,148

(22) Filed: Jul. 31, 2003

(65) Prior Publication Data

US 2004/0024205 A1 Feb. 5, 2004

(30) Foreign Application Priority Data

Aug. 1, 2002 (FR) .................................. 02 09820

(51) Int. Cl.
- C07D 295/00 (2006.01)
- C07D 265/30 (2006.01)
- C07D 295/02 (2006.01)
- C07D 241/04 (2006.01)
- C07D 233/56 (2006.01)

(52) U.S. Cl. ..................... 540/612; 544/178; 544/404; 548/335.1; 548/373.1

(58) Field of Classification Search ................ 540/612; 544/178, 404; 548/335.1, 373.1
See application file for complete search history.

(56) References Cited

U.S. PATENT DOCUMENTS 5,164,497 A * 11/1992 King et al. .................... 544/87
5,453,516 A * 9/1995 Fischer et al. .............. 548/543

FOREIGN PATENT DOCUMENTS

| JP | 09169737 | 6/1997 |
| WO | 9608537 | 3/1996 |

OTHER PUBLICATIONS

Smith and Linnhoff, "The Design of Separators in the Context of Overall Processes" Chemical Engineering Research and Design, vol. 66, pp. 195-228 (May 1988).*
Lissel, "N-Methylierung . . . Derivaten", Liebigs Annalen Der Chemie, Verlag Chemie GmbH, Weinheim, 1987, pp. 77-79.

* cited by examiner

Primary Examiner—James O. Wilson
Assistant Examiner—Zachary C. Tucker
(74) Attorney, Agent, or Firm—Charles A. Muserlian

(57) ABSTRACT

A process for the monomethylation of nitrogenous heterocycles having at least one nitrogen atom bonded to a hydrogen atom by reacting the nitrogenous heterocycle with dimethyl carbonate at a temperature of between 100° and 200° C. and a pressure of between $0.93 \times 10^5$ Pa and $1.07 \times 10^5$ Pa while methanol produced during the reaction is distilled off as it is formed.

9 Claims, No Drawings

MONOMETHYLATION OF NITROGENEOUS HETEROCYCLES

A process for the monomethylation of nitrogenous heterocycles which heterocycles, such as the family of the azoles, have applications in various fields, such as agrochemicals, pharmaceuticals, biotechnologies, paints and dyes.

STATE OF THE ART

Known processes for the N-methylation of nitrogenous heterocyles consist of alkylating nitrogenous heterocycles with alkyl halides or alkyl sulfates which processes exhibit numerous disadvantages. Some reactants, such as dimethyl sulfate, are highly toxic and furthermore, the product obtained requires a complex purification process. Processes using reactants which are less toxic to the environment were consequently provided and several processes for methylation with dimethyl carbonate were envisaged.

The authors of a paper which appeared in Liebigs Ann. Chem. (Liebigs Ann. Chem., 1987, 1, 77) describe a process for the N-methylation of imidazole, benzimidazole and their derivatives by reaction of the nitrogenous heterocycle with dimethyl carbonate in the presence of a base (potassium carbonate) and of a phase transfer catalyst (the crown ether 18-crown-6). The disadvantages of such a synthesis are the high cost and the toxicity of the crown ether. Furthermore, an operation for separating the catalyst from the reaction medium is necessary at the end of the reaction.

A process disclosed in Patent No. WO 96/08537, which does not involve a crown ether, was then provided. This process consists in producing organic pigments by methylating heterocycles with dimethyl cabonate in the presence of alkaline earth carbonates or hydroxides. The reaction is carried out at a temperature of between 80° C. and 150° C. at atmospheric pressure. In point of fact, the yield remains low, even in the presence of a catalyst.

Another process, disclosed in Patent JP 9169737, provides a process for the synthesis of N-methylated imidazoles by reaction, at a temperature of between 120° C. and 200° C., preferably at 160° C., of the imidazole with dimethyl carbonate. The process disclosed is restricted only to the synthesis of methylimidazole derivatives from compounds which have boiling points in the vicinity of 250° C. Tests carried out with heterocycles having lower boiling points show that this process cannot be generalized to all nitrogenous heterocycles and in particular, to nitrogeneous heterocycles having a boiling point of less than 190° C.

OBJECTS OF THE INVENTION

It is an object of the invention to provide a simple, economical process for the preparation of N-methylation of nitrogenous heterocycles which is selective for producing only monomethylated products.

This and other objects and advantages of the invention will become obvious from the following detailed description.

THE INVENTION

The novel process of the invention for monomethylation of nitrogenous heterocycles containing at least one nitrogen atom bonded to a hydrogen atom comprises reacting said nitrogen heterocycle with dimethyl carbonate at 100° C. to 200° C. and a pressure of $0.93 \times 10^5$ Pa to $1.07 \times 10^5$ Pa while continuously removing the methanol produced.

This process, carried out at a temperature of between 100° C. and 200° C. and at approximately atmospheric pressure, exhibits the advantage of being simple to carry out. Furthermore, the fact of withdrawing the methanol continuously, that is to say by distilling it off as it is formed, makes it possible to control the temperature of the reaction medium. This has several advantages. The process can thus be applied to several families of nitrogenous heterocycles and not only to heterocycles having a high boiling point of the order of 250° C. This also makes it possible to add a large amount of dimethyl carbonate to the reaction medium without lowering the temperature thereof. As the reaction kinetics are a function of the amount of dimethyl carbonate in the reaction medium, the reaction is carried out with very good kinetics.

This process applies not only to heterocycles having a boiling point of the order of 190° C. or greater than 190° C., of the order of 250° C., but also to heterocyclcles having lower boiling points, of the order of 120° C. Generally, the process applies to heterocycles having a boiling point of greater than or equal to 120° C.

Preferably, the nitrogenous heterocycles are chosen from azoles and their benzene derivatives, indoline, pyrazolidine, morpholine, piperazine and azepine. The term "azoles" is used to refer to five-membered heterocyclic compounds, at least one nitrogen atom of which is bonded to a hydrogen atom. Mention may be made, as azoles comprising one nitrogen atom, of indole and carbazole and, as azoles comprising two nitrogen atoms, of imidazole, benzimidazole, pyrazole and indazole. The azoles comprising three nitrogen atoms are in particular triazoles and benzotriazoles and the azole comprising five nitrigen atoms is pentazole.

The amount of dimethyl carbonate used is between 1 and 5 mol per mole of nitrogenous heterocycle and preferably between 1.2 and 3 mol per mole of nitrogeneous heterocycle. The dimethyl carbonate is generally added gradually to the reaction medium, with a flow rate of between 0.001 mol/mol of substrate. h and 1 mol/mol of substrate.h, the substrate being the nitrogenous heterocycle.

The reaction was carried out at a temperature of between 100° C. and 200° C. and preferably between 120° C. and 180° C. The reaction is carried out at a pressure of between $0.93 \times 10^5$ Pa and $1.07 \times 10^5$ Pa, i.e. at a pressure of between 700 mm/Hg and 800 mm/Hg. Generally, the local atmospheric pressure is within this range and the reaction is carried out at this pressure.

The nitrogeneous heterocyle is monomethylated on the nitrogen atom bonded to a hydrogen atom. When the nitrogenous heterocycle comprises more than one nitrogen atom, that is to say at least two nitrogen atoms, each nitrogen atom being bonded to a hydrogen atom, the reaction is selective. This means that the product undergoes a single methylation and thus that only the monomethylated product is synthesized. For this, the monomethylated product is continuously withdrawn, that is to say removed from the reaction medium as it is formed. When the nitrogenous heterocycle comprises at least two nitrogen atoms, each being bonded to a hydrogen atom, the process can be carried out in the presence of a solvent. Examples of the solvent are chosen from the group consisting of methoxy-naphthalene, anisole and trichlorobenzene.

A preferred embodiment of the invention is now given. To do this, use is made of a reactor equipped with a stirring system and a thermometer and surmounted by a distillation column and with a reflux condenser.

First, the nitrogenous heterocycle is introduced, either alone or with a portion of the amount of dimethyl carbonate which will be used during the reaction. The reaction medium is subsequently heated to a temperature of between 100° C. and 200° C., preferably between 120° C. and 180° C.

As the process is continuous or semicontinuous, the dimethyl carbonate is subsequently introduced into the reaction medium with a flow rate of between 0.001 and 1 mol/mol of substrate.h, the substrate being the nitrogenous heterocycle. The nitrogenous heterocycle can also be introduced continuously, as a mixture with dimethyl carbonate, with a dimethyl carbonate-nitrogenous heterocycle molar ratio of between 1 and 10, preferably between 1 and 3.

The methanol produced during the reaction is distilled off as it is formed. At the end of the reaction, the reaction medium is allowed to cool to ambient temperature and the methylated product is recovered. When the nitrogenous heterocycle comprises at least two nitrogen atoms, each bonded to a hydrogen atom, the monomethylated product formed is also withdrawn as it is formed.

The examples which follow illustrate, without implied limitation, alternative embodiments of the invention.

EXAMPLE 1

Synthesis of 1-methylimidazole

The reaction was carried out in a 250 ml reactor equipped with a stirrer, a thermometer and a feed system so that it was possible to feed it continuously throughout the reaction. The reactor was surmounted by the distillation column, with a reflux ratio head and a reflux condenser.

34.04 g of imidazole, i.e. 0.5 mol, were introduced into the reactor and the medium was then heated to 170° C. and this temperature was maintained throughout the reaction. The dimethyl carbonate was introduced into the reactor with a flow rate of 145 mmol/h over 7 hours. The methanol produced was distilled off as it was formed. After having introduced all the dimethyl carbonate, the reaction was continued for 2 hours at 170° C. The reaction medium was then allowed to cool to ambient temperature to obtain 33.36 g of 1-methylimidazole, i.e. 0.49 mol, which corresponded to a yield of 98%.

EXAMPLE 2

Synthesis of N-methylmorpholine

The reactor used was the same as that described in Example 1. 100 g of 2-methoxynaphthalene were introduced into the reactor and then, the medium was heated to 170° C. and maintained throughout the reaction. A morpholine/dimethyl carbonate mixture was then introduced in a molar ratio of ½ and with a morpholine flow rate of 72 mmol/h. The time for introducing the morpholine/dimethyl carbonate mixture was 7 hours and then, the dimethyl carbonate alone was introduced into the reactor with a flow rate of 100 mmol/h for 2 hours. The methanbol and the N-methylmorpholine were withdrawn continuously to obtain 22.25 g of N-methylmorpholine, i.e. 0.22 mol, which corresponded to a yield of 43%.

EXAMPLE 3

Synthesis of N-methylpiperazine

The apparatus used was the same as that described in Example 1. 43.07 g of piperazine, i.e. 0.5 mol, were introduced into the reactor and the medium was then heated to 110° C. and this temperature was maintained throughout the reaction. The dimethyl carbonate was introduced into the reactor with a flow rate of 100 mmol/h for 10 hours.

The methanol produced was distilled off as it was formed and the excess dimethyl carbonate was also distilled off, to stabilize the temperature of the reactor medium at 110° C. The reaction medium was then allowed to cool to ambient temperature to obtain 14.52 g of 1-methyl piperazine, i.e. 0.145 mol, which corresponded to a yield of 29%.

EXAMPLE 4

Synthesis of N-methylpyrazole

The apparatus used is the same as that described in Example 1. 20.64 g of pyrazole, i.e. 0.3 mol, and 4.5 g of dimethyl carbonate, i.e. 0.05 mol, were introduced into the reactor. The medium was then heated to 140° C. and this temperature was maintained throughout the reaction. The dimethyl carbonate was introduced into the reactor with a flow rate of 60 mmol/h for 8 hours and the methanol produced was distilled off as it was formed. The reaction medium was then allowed to cool to ambient temperature to obtain 17.24 g of N-methyyl pyrazole i.e. 0.21 mol, which corresponded to a yield of 70%.

EXAMPLE 5

Synthesis of 1,3,5-trimethylpyrazole from 3,5-dimethylpyrazole

The apparatus used was the same as that described in Example 1. 24.03 g of 3,5-dimethylpyrazole, i.e. 0.25 mol, and 4.5 g of dimethyl carbonate, i.e. 0.05 mol, were introduced and the reaction medium was heated to 140° C. and this temperature was maintained throughout the reaction. The dimethyl carbonate was then introduced with a flow rate of 50 mmol/h for 8 hours. The methanol produced was distilled off as it was formed and the excess dimethyl carbonate was also distilled off to stabilize the temperature of the reaction medium at 140° C. After having introduced all the dimethyl carbonate, the reaction medium was allowed to cool to ambient temperature to obtain 15.41 g of 1,3,5-trimethylpyrazole, i.e. 0.14 mol, which corresponded to a yield of 57%.

The example which follows does not form part of the invention. It was carried out for the purpose of showing that the continuous withdrawal of the methanol produced during the reaction is necessary to be able to generalize this process to several families of nitrogenous heterocycles and particularly, to nitrogenous heterocycles having a boiling point of less than 190° C.

EXAMPLE 6

Synthesis of N-methylpyrazole without Withdrawal of the Methanol

The apparatus used is the same as that described in Example 1. 20.64 g of pyrazole, i.e. 0.3 mol, and 4.5 g of dimethyl carbonate, i,e. 0.05 mol, were introduced into the reactor. The medium was then heated to 140° C. and then the dimethyl carbonate was introduced into the reactor with a flow rate of 60 mmol/h (i.e. 5.4 g/h) for 8 hours. The methanol formed was not withdrawn.

It was found that the temperature of the reaction medium remained stable at 140° C. for 1 hour and then gradually decreased to 115° C. at the end of the reaction. The reactor medium was then allowed to cool to ambient temperature to obtain only 3.53 g of N-methylpyrazole, i.e. 0.042 mol, which corresponded to a yield of 14%.

The N-methylpyrazole was therefor obtained with a markedly lower yield (14%) than that obtained with the process which is a subject matter of the invention, with withdrawal of the methanol (yield of 70%, Example 4).

Various modifications of the process of the invention may be made without departing from the spirit or scope thereof. It is to be understood that the invention is intended to be limited only as defined in the appended claims.

What we claim is:

1. A process for the N-monomethylation of nitrogenous heterocycles having at least one nitrogen atom bonded to a hydrogen atom comprising reacting said heterocycle with dimethyl carbonate at a temperature of between 100° C. and 200° C. and at a pressure of between 0.93 to $10^5$ Pa and $1.07 \times 10^5$ Pa while continuously withdrawing the methanol produced during the reaction.

2. The process of claim 1, wherein the nitrogenous heterocycles have a boiling point of at least equal to 120° C.

3. The process of claim 2, wherein the nitrogenous heterocycles are selected from the group consisting of azoles and benzene derivatives thereof, indoline, pyrazolidine, morpholine, piperazine and azepine.

4. The process of claim 1, wherein the reaction is carried out at a temperature of between 120° C. and 180° C.

5. The process of claim 1, wherein the amount of dimethyl carbonate is between 1 and 5 mole per mole of nitrogenous heterocycle.

6. The process of claim 1, wherein the dimethyl carbonate is added to the reactor medium over a period of time.

7. The process of claim 6, wherein the dimethyl carbonate is introduced into the reactor medium with a flow rate of between 0.001 mol/mol of nitrogenous heterocycle per hour and 1 mol/mol of nitrogenous heterocycle per hour.

8. A process for the N-monomethylation of nitrogenous heterocycles having at least one nitrogen atom bonded to a hydrogen atom comprising reacting said heterocycle with dimethyl carbonate at a temperature of between 100° C. and 200° C. and at a pressure of between 0.93 to $10^5$ Pa and $1.07 \times 10^5$ Pa while continuously withdrawing the methanol produced during the reaction wherein the nitrogenous heterocycle comprises at least two nitrogen atoms each bonded to a hydrogen atom.

9. The process of claim 8, wherein the monomethylated nitrogenous heterocycle is continuously withdrawn.

* * * * *